United States Patent [19]

Dickore et al.

[11] 4,426,523

[45] Jan. 17, 1984

[54] PREPARATION OF 1-AMINO-1,3,5-TRIAZINE-2,4(1H, 3H)-DIONES

[75] Inventors: Karlfried Dickore, Leverkusen; Engelbert Kühle, Bergisch-Gladbach, both of Fed. Rep. of Germany

[73] Assignee: Bayer Aktiengesellschaft, Leverkusen, Fed. Rep. of Germany

[21] Appl. No.: 346,341

[22] Filed: Feb. 5, 1982

[30] Foreign Application Priority Data

Feb. 24, 1981 [DE] Fed. Rep. of Germany ....... 3106724

[51] Int. Cl.³ .......................................... C07D 251/38
[52] U.S. Cl. .................................................. 544/223
[58] Field of Search ........................................ 544/223

[56] References Cited

U.S. PATENT DOCUMENTS 3,907,796 9/1975 Jewell et al. ......................... 544/194
3,950,367 4/1976 Botta .................................... 544/223
4,356,024 10/1982 Dickore et al. ...................... 544/223

FOREIGN PATENT DOCUMENTS 34751 9/1981 European Pat. Off. .
1259871 2/1968 Fed. Rep. of Germany .
2254200 5/1974 Fed. Rep. of Germany .

Primary Examiner—John M. Ford
Attorney, Agent, or Firm—Sprung, Horn, Kramer & Woods

[57] ABSTRACT

Herbicidal 1-amino-1,3,5-triazine-2,4(1H, 3H)-diones of the general formula

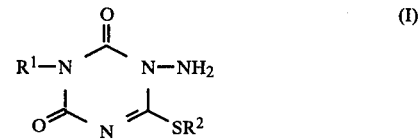

are obtained in good yields if an N-substituted O-aryl N-chlorocarbonyl carbamate of the general formula

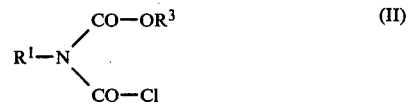

is reacted with an isothiosemicarbazone of the general formula

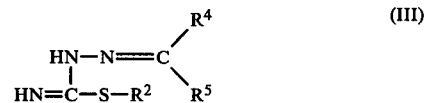

or hydrohalide thereof, ($R^1$ to $R^4$ in formulae (I) to (III) having the meanings given in the description), at a temperature between 0° and 50° C., in the presence of an acid-binding agent, the open-chain intermediate products formed thereby are then heated (if appropriate without intermediate isolation), in a second stage, to a temperature between 50° and 150° C. and, finally, in a third stage, the 1-alkylideneamino-1,3,5-triazine-2,4(1H, 3H)-dione formed thereby is hydrolyzed (if appropriate again without intermediate isolation) in an acid medium.

8 Claims, No Drawings

PREPARATION OF 1-AMINO-1,3,5-TRIAZINE-2,4(1H, 3H)-DIONES

The present invention relates to an unobvious process for the production of certain herbicidal 1-amino-1,3,5-triazine-2,4-(1H, 3H)-diones, some of which are known.

It has already been disclosed that 1-amino-1,3,5-triazine-2,4(1H, 3H)-diones can be prepared by the reaction of imidodicarboxylic acid dichlorides with hydrohalides of isothiosemicarbazones and subsequent acidcatalyzed hydrolysis of the 1-alkylideneamino derivatives first formed as intermediate products (see U.S. Pat. No. 4,056,527). However, this process has a number of disadvantages. Thus, the use of imidodicarboxylic acid dichlorides as starting materials represents considerable technical effort, since their preparation is only possible by multi-stage processes (see U.S. Pat. No. 3,962,327) or via starting materials which are difficult to obtain (see DE-OS (German Published Specification) No. 1,298,095), and, in addition, the yields are not satisfactory. A further disadvantage of the known process consists in the fact that the ring closure of imidodicarboxylic acid dichlorides with the hydrohalides of isothiosemicarbazones has to be carried out in the presence of three mols of an organic base in an organic solvent. Carrying out this process industrially is made difficult, in addition, by the necessary recovery of the solvent and the organic base.

According to the present invention we provide a process for the production of a 1-amino-1,3,5-triazine-2,4(1H, 3H)-dione of the general formula

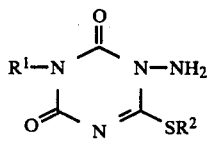

(I)

in which $R^1$ represents a saturated or unsaturated aliphatic or cycloaliphatic hydrocarbon radical, an araliphatic hydrocarbon radical or an aryl radical, each of which is optionally substituted by one or more substituents selected from halogen, nitro, alkyl, alkoxy, alkylmercapto, halogeno-alkyl, cyano, aryl, aryloxy and arylmercapto, or represents a heterocyclic radical, and $R^2$ represents a saturated or unsaturated aliphatic or cycloaliphatic hydrocarbon radical or an araliphatic hydrocarbon radical, each of which is optionally substituted by one or more substituents selected from halogen, cyano, nitro, alkyl, alkoxy, alkoxycarbonyl and alkylmercapto, characterized in that, in a first stage, an N-substituted O-aryl N-chlorocarbonyl-carbamate of the general formula

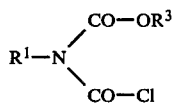

(II)

in which $R^1$ has the meaning given above and $R^3$ represents an aryl radical, which is optionally substituted by one or more substituents selected from alkyl, alkoxy, halogen, halogenoalkyl, cyano and nitro, is reacted with an isothiosemicarbazone of the general formula

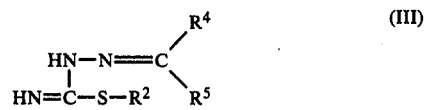

(III)

in which $R^2$ has the meaning given above, $R^4$ represents a hydrogen atom, or an alkyl radical, a cycloalkyl radical, an aralkyl radical or an aryl radical each of which is optionally substituted by halogen, cyano, nitro, alkyl, alkoxy or alkyl-mercapto, and $R^5$ represents an alkyl radical, a cycloalkyl radical, an aralkyl radical or an aryl radical, each of which is optionally substituted by halogen, cyano, nitro, alkyl, alkoxy or alkylmercapto, or $R^4$ and $R^5$, together with the alkylidene C atom, form a 5-membered to 7-membered carbocyclic ring, or a hydrohalide thereof, at a temperature between 0° and 50° C., in the presence of an acid-binding agent and, if appropriate, in the presence of a diluent, the open-chain intermediate products, which are formed thereby, of the general formula

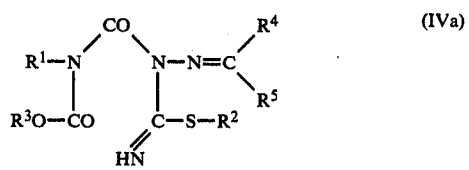

(IVa)

and/or

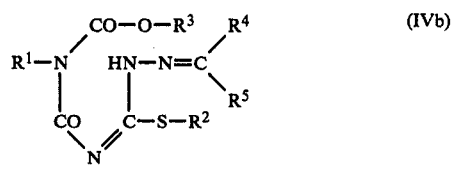

(IVb)

are then heated, if appropriate without intermediate isolation, in a second stage, to a temperature between 50° and 150° C., if appropriate in the presence of a diluent, and finally, in a third stage, the 1-alkylideneamino-1,3,5-triazine-2,4(1H, 3H)-dione, which is formed thereby, of the general formula

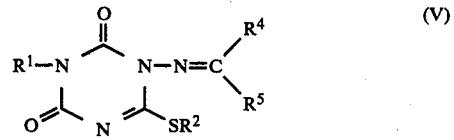

(V)

in which $R^1$, $R^2$, $R^4$ and $R^5$ have the meaning given above, is hydrolyzed in an acid medium, if desired without intermediate isolation. The process according to the present invention allows compounds of formula (I) to be obtained in high yields, in a technically simple manner.

In comparison with the previously known process, the process according to the invention has the advantage that only 1 mol (or 2 mols if a hydrogen halide of (III) is employed) of an acid-binding agent is required. The N-substituted O-aryl N-chlorocarbonyl carbamates used as starting materials in the process according to the invention are available in a simple manner from precursors which are readily obtainable industrially, for example by phosgenation of N-substituted O-aryl carbamates (see DE-AS (German Published Specification) No. 1,259,871).

If O-phenyl N-chlorocarbonyl-N-neopentyl carbamate and acetone-S-ethylisothiosemicarbazone are used as starting materials, the course of the reaction according to the present invention is illustrated by the following equation:

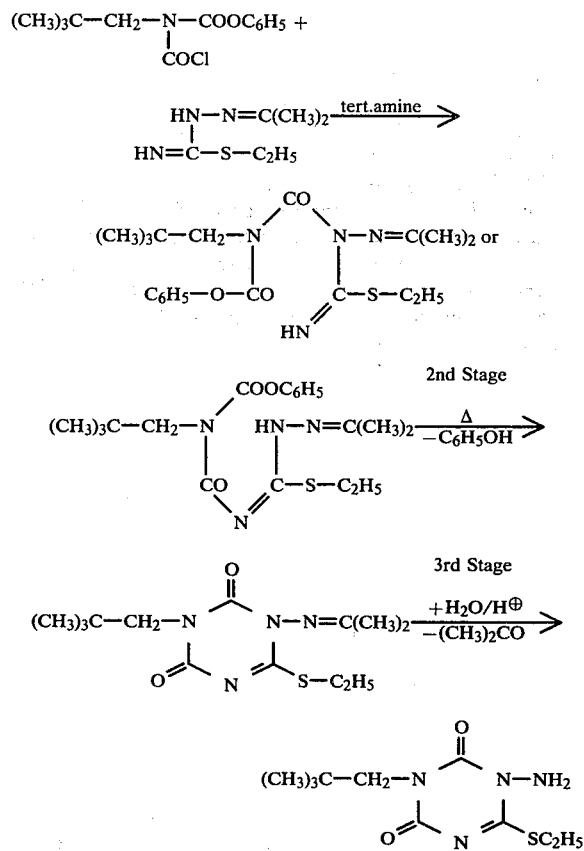

Preferred N-substituted O-aryl N-chlorocarbonyl carbamates of formula (II) to be used as starting materials are those,
in which $R^1$ represents a straight or branched alkyl radical which has 1 to 10 carbon atoms and which can be optionally substituted by lower alkoxy, lower alkylmercapto, halogen (particularly chlorine or fluorine), cyano and nitro; and also an alkenyl radical having 3 to 8 carbon atoms, an alkinyl radical having 3 to 8 carbon atoms and a cycloaliphatic radical having 5 to 8 ring carbon atoms, which radical can be optionally substituted by lower alkyl or lower alkoxy; an araliphatic radical having 7 to 12 carbon atoms, it being possible for the aromatic ring system to be optionally substituted by halogen, nitro, trihalogeno-lower alkyl (particularly trifluoromethyl), cyano, lower alkyl, lower alkoxy or lower alkylmercapto; an aromatic radical which has 6 to 12 carbon atoms and which can be optionally substituted by halogen, nitro, trihalogeno-lower alkyl (particularly trifluoromethyl), cyano, lower alkyl, lower alkoxy or lower alkylmercapto; or a heterocyclic radical having 5 or 6 ring atoms, it being possible for 1 to 3 hetero atoms (such as oxygen, sulphur and/or nitrogen) to be present in the ring system; and $R^3$ represents a phenyl radical which can be optionally substituted by lower alkyl, lower alkoxy, halogen, halogeno-lower alkyl (particularly trifluoromethyl), cyano and/or nitro, or naphthyl radical.

Preferred isothiosemicarbazones of formula (III) to be employed, in addition, as starting materials are those, in which $R^2$ represents a straight or branched alkyl radical which has 1 to 6 carbon atoms and which can be optionally substituted by lower alkoxy, lower alkylmercapto, lower alkoxycarbonyl, halogen, cyano or nitro; an alkenyl radical having 3 to 6 carbon atoms; an alkinyl radical having 3 to 6 carbon atoms; a cycloaliphatic radical which has 5 to 8 ring carbon atoms and which can be optionally substituted by lower alkyl or lower alkoxy; or an araliphatic radical having 7 to 12 carbon atoms, it being possible for the aromatic ring system to be optionally substituted by one or more substitutents selected from lower alkyl, lower alkoxy, lower alkylmercapto, lower alkoxycarbonyl, halogen, cyano and nitro, $R^4$ represents a hydrogen atom or an alkyl radical having 1 to 3 carbon atoms, a cycloalkyl radical having 5 to 7 carbon atoms, or a benzyl or aryl radical having 6 to 10 carbon atoms, it being possible for each of the mentioned radicals to be substituted by halogen, cyano, nitro, lower alkyl, lower alkoxy or lower alkylmercapto, and $R^5$ represents an alkyl having 1 to 3 carbon atoms, cycloalkyl having 5 to 7 carbon atoms, a benzyl or aryl radical having 6 to 10 carbon atoms, it being possible for each of the mentioned radicals to be substituted by halogen, cyano, nitro, lower alkyl, lower alkoxy or lower alkylmercapto, or $R^4$ and $R^5$ together with the alkylidene C atom form a 5-membered to 7-membered carbocyclic ring.

$R^4$ and $R^5$ particularly preferably represent methyl radicals.

The expressions such as "lower alkyl", "lower alkoxy", "lower alkylmercapto" and "halogeno-lower alkyl" for the purposes of the present invention denote the corresponding radicals, each having 1–4 C atoms.

Some of the O-aryl N-chlorocarbonyl carbamates (II) which are used according to the invention as starting materials are known and can be prepared by the reaction of an N-substituted aryl carbamate of the general formula

$$R^1\text{—NH—CO—OR}^3 \qquad \text{(VI)}$$

in which $R^1$ and $R^3$ have the meaning given above, with phosgene in the presence of a tertiary aromatic amine (see DE-AS (German Published Specification) 1,259,871), or by the reaction of a bis-chlorocarbonyl-amine of the general formula

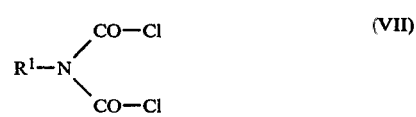

in which $R^1$ has the meaning given above, with a phenol of the general formula

HO—R³            (VIII)

in which

R³ has the meaning given above, in the presence of a tertiary amine, in the molar ratio 1:1 (see DE-OS (German Published Specification) No. 2,142,496). In addition, the starting compounds of the formula (II) are obtained by phosgenation of an N-substituted aryl carbamate of formula (IV), without the addition of an acid-binding agent, at a temperature between 100° and 200° C., preferably at 130° to 180° C., if appropriate in the presence of an inert solvent as the diluent; hydrocarbons (such as toluene or xylene) or chlorohydrocarbons (such as chlorobenzene or dichlorobenzene) are examples of suitable solvents of this type. This latter process is advantageously used if the N-substitutent of the carbamic acid ester is highly branched, for example isopropyl, isobutyl or neopentyl N-substituents (see the examples hereinbelow).

Aryl carbamates of formula (VI) are already known and can be prepared, according to known processes, by the addition of isocyanates onto phenols (see Houben-Weyl, Methoden der organischen Chemie (Methods of Organic Chemistry), 4th edition, volume 8, page 142 (1952)), or by the reaction of carbonic acid aryl ester chlorides with primary amines (see Houben-Weyl, Methoden der organischen Chemie (Methods of Organic Chemistry), 4th edition, volume 8, page 138 (1952) and the Preparative Examples). The starting compounds of the formula (VI) can also be prepared by the reaction of diaryl carbonates with amines (see Houben-Weyl, Methoden der organischen Chemie (Methods of Organic Chemistry), 4th edition, volume 8, page 139 (1952)).

The following may be individually mentioned as examples of the N-substituted O-aryl N-chlorocarbonyl carbamates of formula (II) which can be used in the process according to the present invention:

the phenyl ester, 2-chlorophenyl ester, 4-chlorophenyl ester, 4-methylphenyl ester, 4-methoxyphenyl ester, 4-nitrophenyl ester, 1-naphthyl ester or 2-naphthyl ester of methylcarbamic acid, ethylcarbamic acid, 2-chloroethylcarbamic acid, 2,2,2-trifluoroethylcarbamic acid, propylcarbamic acid, isopropylcarbamic acid, tert.-butylcarbamic acid, sec.-butylcarbamic acid, isobutylcarbamic acid, pentylcarbamic acid, isopentylcarbamic acid, neopentylcarbamic acid, 1-ethylpropylcarbamic acid, 1,2,2-trimethylpropylcarbamic acid, 2-ethoxymethylcarbamic acid, 2-ethylmercaptoethylcarbamic acid, ω-cyanohexylcarbamic acid, allylcarbamic acid, propargylcarbamic acid, cyclopropylmethylcarbamic acid, cyclopentylmethylcarbamic acid, cyclohexylmethylcarbamic acid, (2,5-methano-cyclohexyl)-methylcarbamic acid, cycloheptylmethylcarbamic acid, cyclododecanylmethylcarbamic acid, adamantylmethylcarbamic acid, 2-furylmethylcarbamic acid, 2-pyranylmethylcarbamic acid, 2-pyridylmethylcarbamic acid, 3-pyridylmethylcarbamic acid, 4-pyridylmethylcarbamic acid, 2-methylpentylcarbamic acid, 2-ethylpentylcarbamic acid, 2-methylhexylcarbamic acid, 2-ethylhexylcarbamic acid, cyclopentylcarbamic acid, cyclohexylcarbamic acid, 2-methylcyclohexylcarbamic acid, benzylcarbamic acid, 4-chlorobenzylcarbamic acid, 4-nitrobenzylcarbamic acid, phenethylcarbamic acid, phenylcarbamic acid, 3-chlorophenylcarbamic acid, 4-chlorophenylcarbamic acid, 3,5-dichlorophenylcarbamic acid, 3,4-dichlorophenylcarbamic acid, 3-trifluoromethylphenylcarbamic acid, 2-chloro-4-nitrophenylcarbamic acid, 3-methylphenylcarbamic acid, 4-methylphenylcarbamic acid, 3-methoxyphenylcarbamic acid, 1-naphthylcarbamic acid, 2-furylcarbamic acid, 4-pyridylcarbamic acid, 2-thienylcarbamic acid, 2-benzthiazolylcarbamic acid or 2-benzimidazolylcarbamic acid.

The isothiosemicarbazones, or hydrohalides thereof, of the formula (III), which are further to be used according to the invention as starting materials, are also known and can be prepared according to known processes, for example by S-alkylation of thiosemicarbazones (see Houben-Weyl, Methoden der organischen Chemie (Methods of Organic Chemistry), 4th edition, volume 9, page 912).

The following may be individually mentioned as examples of such isothiosemicarbazones of formula (III): acetone-S-methylisothiosemicarbazone, acetone-S-ethylisothiosemicarbazone, acetone-S-benzylisothiosemicarbazone, acetone-S-carbomethoxymethylisothiosemicarbazone, isobutyraldehyde-S-methylisothiosemicarbazone, benzaldehyde-S-methylisothiosemicarbazone, benzaldehyde-S-2-chloroethylisothiosemicarbazone, acetone-S-allylisothiosemicarbazone, acetone-S-propargylisothiosemicarbazone, acetone-S-methoxymethylisothiosemicarbazone, acetone-S-cyanomethylisothiosemicarbazone, cyclopentanone-S-methylisothiosemicarbazone, cyclohexanone-S-ethylisothiosemicarbazone, cyclohexanone-S-carbethoxymethylisothiosemicarbazone, cycloheptanone-S-ethylisothiosemicarbazone, acetophenone-S-ethylisothiosemicarbazone, benzophenone-S-methylisothiosemicarbazone, butan-2-one-S-4-chlorobenzylisothiosemicarbazone, or butan-2-one-S-ethylisothiosemicarbazone, and hydrochlorides and hydrobromides thereof.

A particularly preferred combination of reactants is O-phenyl N-chlorocarbonyl-N-neopentyl carbamate, and S-ethylacetoneisothiosemicarbazone, or a hydrochloride or hydrobromide thereof, as starting materials of formulae (II) and (III), respectively.

The first and second stage of the process according to the invention, that is to say the acylation reaction (II)+(III)→(IVa) or (IVb) and the ring closure reaction (IVa/(IVb)→(V), are preferably carried out in the presence of an inert organic solvent as the diluent. Hydrocarbons (such as toluene), chlorinated hydrocarbons (such as chlorobenzene) or alcohols (such as isopropanol and sec.-butanol) are suitable for this purpose. The same solvent is advantageously used for both stages.

The first process stage (acylation) is carried out with the addition of an acid-binding agent. Tertiary amines (such as triethylamine or pyridine) or inorganic bases (such as sodium carbonate or sodium hydroxide) can be used as the acid-binding agent. If the free base of formula (III) is employed, the reaction is carried out with the molar ratio 1:1, and if the hydrohalide of formula (III) is used, the acid-binding agent is employed in the molar ratio 2:1.

The reaction temperatures can be varied within a wide range, i.e. the first process stage is carried out, at a temperature between 0° and 50° C., preferably at between 5° and 35° C. The second process stage is carried out at a temperature between 50° and 150° C., preferably between 70° and 120° C. In general, the use of elevated pressure is not necessary.

In carrying out the process according to the invention, 0.9 to 1.1 mols of the isothiosemicarbazone of the formula (III), or the hydrohalide thereof, is employed, in general, per mol of the O-aryl N-chloro-carbonyl carbamate of the formula (II); the components are preferably reacted in the stoichiometric molar ratio 1:1.

The compounds of the formula (IVa) or (IVb), which are formed as intermediate products, and the 1-alkylidenamino-1,3,5-triazine-2,4(1H, 3H)-diones of the formula (V) can each be isolated at an intermediate stage, if desired. The working-up and isolation of the intermediate products of formula (V) can be effected, for example, by distilling off in vacuo the optionally substituted phenol formed in the cyclization reaction, and purifying the residue, if necessary, by distillation in a high vacuum or by dissolving and allowing to crystallize (see examples hereinbelow).

The subsequent hydrolysis, for splitting off the alkylidene radical ($=CR^4R^5$) which serves as a protective group, (V)→(I), is carried out in an acid medium, in a manner which is in itself known (see, for example, DE-OS (German Published Specification) No. 2,254,200 or U.S. Pat. No. 4,056,527). It is particularly advantageous to dissolve the intermediate products of formula (V) in an alcohol (such as isopropanol) and to add a catalytic quantity of an acid (for example a mineral acid, such as sulphuric acid, or an organic sulphonic acid, such as p-toluenesulphonic acid) to the solution, at a temperature between 40° and 70° C., if appropriate under reduced pressure, and to distil off from the reaction mixture the resulting carbonyl compound of the formula $R^4$—CO—$R^5$, together with a part of the alcohol employed as the diluent. The isolation of the end product (I) is effected in a known manner, by crystallizing out the product and filtering it off; for further purification, the end products of formula (I) can easily be recrystallized.

The 1-amino-1,3,5-triazine-2,4(1H, 3H)-diones of formula (I) which can be prepared according to the invention are for the most part known and have excellent herbicidal properties (see, for example, DE-OS (German Published Specification) No. 2,254,200; U.S. Pat. No. 4,056,527; and also Danish Patent Specification 136,067).

The active compounds according to the invention influence plant growth and can therefore be used as defoliants, desiccants, agents for destroying broad-leaved plants, germination inhibitors and, especially, as weed-killers. By "weeds" in the broadest sense there are meant plants growing in places where they are not desired.

Whether the compounds according to the invention act as total herbicides or selective herbicides depends essentially on the amount used.

The active compounds according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

The active compounds according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

However, the use of the active compounds according to the invention is in no way restricted to these genera but also embraces other plants, in the same way.

Depending on the concentrations, the compounds can be used for the total combating of weeds, for example on industrial terrain and railway tracks and on paths and squares with or without trees. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

The active compounds can be converted into the customary formulations, such as solutions, emulsions, suspensions, powders, pastes and granules.

These formulations may be produced in known manner, for example by mixing the active compounds with extenders, that is to say liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as aliz-rin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention, as such or in the form of their formulations, can also be used, for combating weeds, as mixtures with known herbicides, finished formulations or tank mixing being possible. Mixture with other known active compounds, such as fungicides, insecticides, acaricides, nematicides, bird repellents, growth factors, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering or dusting.

The active compounds according to the invention can be applied either before or after emergence of the plants. They are preferably applied before emergence of the plants, that is to say by the pre-emergence method. They can also be incorporated into the soil before sowing.

The amount of active compound used can vary within a substantial range. It depends essentially on the nature of the desired effect. In general, the amounts used are between 0.01 and 10 kg of active compound per ha, preferably between 0.05 and 8 kg/ha.

The present invention also provides herbicidal compositions containing as active ingredient a compound of the present invention in admixture with a solid or liquefied gaseous diluent or carrier or in admixture with a liquid diluent or carrier containing a surface-active agent.

The present invention also provides a method of combating weeds which comprises applying to the weeds, or to a habitat thereof, a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier.

It will be seen that the usual methods of providing a harvested crop may be improved by the present invention.

The 1-alkylideneamino-1,3,5-triazine-2,4(1H, 3H)-diones (V), some of which are new, which are formed in the first stage of the process according to the invention are not only of interest as intermediate products for the preparation of the corresponding 1-amino compounds (I), but in addition, themselves have pronounced herbicidal activity (with reference to the known compounds of the general formula (V), also see DE-OS (German Published Specification) No. 2,254,200; U.S. Pat. No. 4,056,527; and Danish Patent Specification No. 136,067).

The new compounds of the general formula (V) can be formulated and used in basically the same manner as that stated previously for compounds of formula (I) prepared by the process of the present invention.

In addition, it is possible to exchange the $SR^2$ radicals located at the 6-position of the compounds of the general formula (I) and (V), by reaction with primary or secondary amines, for alkylamino groups or dialkylamino groups, known herbicidal active compounds likewise being obtained (also see the previously mentioned printed publications: DE-OS (German Published Specification) No. 2,254,200; U.S. Pat. No. 4,056,527; and Danish Patent Specification No. 136,067).

The preparative examples which follow illustrate the invention further.

PREPARATIVE EXAMPLES (A) End products of the formula (I) and intermediate products of the formula (V)

EXAMPLE 1

(a) (3-stage process variant):

1st stage (acylation)

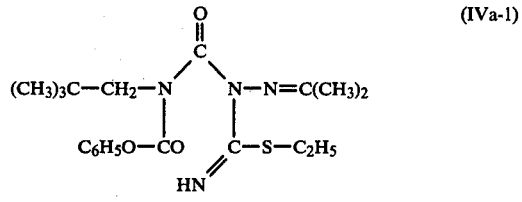
(IVa-1)

and/or

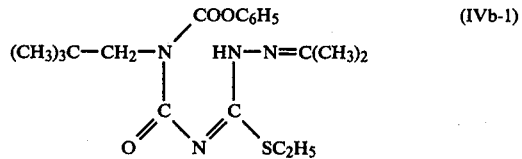
(IVb-1)

53.9 g (0.2 mol) of O-phenyl N-chlorocarbonyl-N-neopentyl carbamate were added to a suspension of 48.0 g (0.2 mol) of S-ethylacetoneisothiosemicarbazone hydrobromide in 250 ml of methylene chloride at 10° C., and 40.4 g (0.4 mol) of triethylamine were added dropwise to the mixture at 10° to 15° C. The mixture was allowed to warm up to 20° C. and was stirred for three hours at this temperature, was extracted several times by shaking with water, and the organic phase was concentrated until crystallization began. The crystals were filtered off under suction at 0° C., and were washed several times with cold methanol, and 48.0 g (61.2% of theory) of a uniform product, of formula (IVa-1) or (IVb-1), of melting point 114°–116° C., were obtained. An unambiguous structure assignment for the acylation product obtained was not possible on the basis of the ¹H-NMR spectrum.

2nd stage (cyclization).

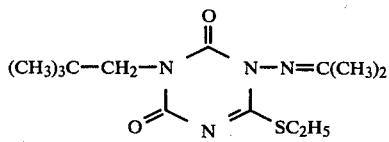
(V-1)

48.0 g (0.122 mol) of the acylation product of formula (IVa-1) or (IVb-1) obtained in the first stage were heated for 5 hours to 120° to 150° C. and the phenol formed was distilled off at a bath temperature of 100° C. and under a pressure of 0.1 mbar, and 34.1 g (93.7% of theory) of 1-isopropylideneamino-6-ethylthio-3-neopentyl-1,3,5-triazine-2,4(1H, 3H)-dione of melting point 100° to 102° C. and of boiling point 176° C./0.4 mbar were obtained as the residue.

3rd stage (hydrolysis)

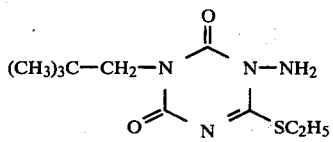
(I-1)

1.1 g of p-toluenesulphonic acid and 5.4 ml of water were added to a solution of 34.1 g (0.114 mol) of 1-isopropylideneamino-6-ethylthio-3-neopentyl-1,3,5-triazine-2,4(1H, 3H)-dione (the compound of formula (V-1)) in 150 ml of isopropanol at 60° C., and the mixture was stirred for one hour at 60° C., the bulk of the reaction product crystallizing out. Approximately 80 ml of the mixture were distilled off at 200 to 300 mbars, the mixture was cooled to 0° C. and was filtered under suction, and the residue was washed with a little methanol. 26.8 g (91% of theory) of 1-amino-6-ethylthio-3-neopentyl-1,3,5-triazine-2,4(1H, 3H)-dione of melting point 202° to 204° C. were obtained.

(b) (2-stage process variant)

1st and 2nd stage 53.9 g (0.2 mol) of O-phenyl N-chlorocarbonyl-N-neopentyl carbamate were added dropwise to a solution of 31.8 g (0.2 mol) of S-ethylacetoneisothiosemicarbazone and 20.2 g (0.3 mol) of triethylamine in 200 ml of toluene at 15° to 20° C. After the mixture had been further stirred for 3 hours, the triethylamine hydrochloride formed was filtered off, the filtrate was boiled for 3 hours under reflux (110° C.), the solvent was evaporated and the phenol formed was distilled off at a bath temperature of 100° C./0.1 mbar. 51.9 g (87% of theory) of 1-isopropylideneamino-6-ethylthio-3-neopentyl-1,3,5-triazine-2,4-(1H, 3H)-dione (the compound of formula (V-1)) of melting point 100°–102° C. were obtained as the residue.

3rd stage

The hydrolysis (V-1)→(I-1) was effected as described in Example 1(a) (3rd stage).

The following 1-alkylideneamino-1,3,5-triazine-2,4(1H, 3H)-diones of formula (V) could be prepared analogously to Examples 1(a) and 1(b)/1st and 2nd stages:

TABLE 1

| Example No. | Structural formula | Compound No. | Melting point (Boiling point) |
| --- | --- | --- | --- |
| (2a) | (CH₃)₂CH—CH₂—N... N—N=C(CH₃)₂ ... SCH₃ | (V-2) | 165° C./0,38 mbar |
| (3a) | CH₃—N... N—N=C(CH₃)(CH₃) ... S—CH₃ | (V-3) | 130–131° C. |
| (4a) | CH₃—N... N—N=C(CH₃)(CH₃) ... S—C₂H₅ | (V-4) | 121–122° C. (173° C./0,5 mbar) |
| (5a) | (CH₃)₂CH—N... N—N=C(CH₃)(CH₃) ... S—CH₃ | (V-5) | 110–112° C. |

TABLE 1-continued

| Example No. | Structural formula | Compound No. | Melting point (Boiling point) |
|---|---|---|---|
| (6a) | (CH₃)₃C—CH₂—N, ring with N—N=C(CH₃)(CH₃), S—CH₃ | (V-6) | 122–124° C. |
| (7a) | CF₃—CH₂—N, ring with N—N=C(CH₃)(CH₃), S—CH₃ | (V-7) | 142° C. (145–150° C./0,3 mbar) |
| (8a) | CF₃—CH₂—N, ring with N—N=C(CH₃)(CH₃), S—C₂H₅ | (V-8) | 112–114° C. |
| (9a) | cyclopentyl-N, ring with N—N=C(CH₃)(CH₃), S—CH₃ | (V-9) | 107–109° C. |
| (10a) | cyclohexyl-N, ring with N—N=C(CH₃)(CH₃), S—CH₃ | (V-10) | 111–112° C. |

The following 1-amino-1,3,5-triazine-2,4(1H, 3H)-diones of formula (I) could be prepared analogously to Examples 1a or 1b/3rd stage:

TABLE 2

| Example No. | Structural formula | Compound No. | Melting point |
|---|---|---|---|
| (2b) | (CH₃)₂CH—CH₂—N, ring with N—NH₂, SCH₃ | (I-2) | 167–169° C. |
| (3b) | CH₃—N, ring with N—NH₂, S—CH₃ | (I-3) | 174–175° C. |
| (4b) | CH₃—N, ring with N—NH₂, S—C₂H₅ | (I-4) | 133–134° C. |
| (5b) | (CH₃)₂CH—N, ring with N—NH₂, S—CH₃ | (I-5) | 148–150° C. |

TABLE 2-continued

| Example No. | Structural formula | Compound No. | Melting point |
|---|---|---|---|
| (6b) | (CH₃)₃C—CH₂—N, N—NH₂, O, N, S—CH₃ (triazine ring with C=O) | (I-6) | 229–231° C. |
| (7b) | CF₃—CH₂—N, N—NH₂, O, N, S—CH₃ (triazine ring) | (I-7) | 147–150° C. |
| (8b) | CF₃—CH₂—N, N—NH₂, O, N, S—C₂H₅ (triazine ring) | (I-8) | 135–137° C. |
| (9b) | cyclopentyl-H—N, N—NH₂, O, N, S—CH₃ (triazine ring) | (I-9) | 158–159° C. |
| (10b) | cyclohexyl-H—N, N—NH₂, O, N, S—CH₃ (triazine ring) | (I-10) | 177–179° C. |

(B) Intermediate products of the formula (VI) and (II)

EXAMPLE 11

(VI-1)

The hitherto unknown O-phenyl N-neopentyl carbamate which was used as a starting compound could be prepared, for example, as follows, using neopentylamine as the starting compound:

A solution of 80 g (2 mols) of sodium hydroxide and 176 g (2 mols) of 99% strength neopentylamine in 3.4 liters of water was added dropwise to a solution of 329 g (2.1 mols) of carbonic acid phenyl ester chloride in 1 liter toluene. An internal temperature of 10° to 20° C. was maintained by cooling. After the reaction had ended, the phases were separated, and the organic phase was washed with water, filtered and evaporated to dryness. 408 g of a 97% strength crude product (95.6% of theory) of melting point 69° to 72° C., sufficiently pure for further reactions, were obtained. After the product had been dissolved in and crystallized from 2 liters of petroleum ether, 365 g of O-phenyl N-neopentyl carbamate (the compound of formula (VI-1)) of melting point 77° to 78° C. were obtained.

EXAMPLE 12

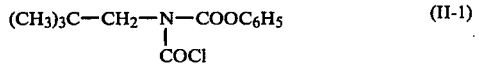

(II-1)

About 150 g of phosgene were passed through a solution of 52 g (0.25 mol) of O-phenyl N-neopentyl carbamate in 250 ml of o-dichlorobenzene, at the boiling point, during the course of 3 hours. After the solvent had been distilled off, 27 g (=40% yield) of O-phenyl N-chlorocarbonyl-N-neopentyl carbamate (the compound of formula (II-1)) of boiling point 129°–135° C./0.133 mbar were obtained by distillation.

It will be understood that the specification and examples are illustrative but not limitative of the present invention and that other embodiments within the spirit and scope of the invention will suggest themselves to those skilled in the art.

We claim:

1. A process for the production of a 1-amino-1,3,5-triazine-2,4(1H, 3H)-dione of the formula

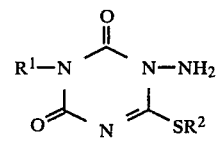

in which

R¹ represents a straight or branched alkyl radical which has 1 to 10 carbon atoms and which can be optionally substituted by lower alkoxy, lower alkylmercapto, halogen (particularly chlorine or fluorine), cyano and nitro; and also an alkenyl radical having 3 to 8 carbon atoms, an alkinyl radical having 3 to 8 carbon atoms and a cycloaliphatic radical having 5 to 8 ring carbon atoms, which radical can be optionally substituted by lower alkyl or lower alkoxy; an araliphatic radical having 7 to 12 carbon atoms, it being possible for the aromatic ring system to be optionally substituted by halogen, nitro, trihalogeno-lower alkyl (particularly trifluoromethyl), cyano, lower alkyl, lower alkoxy or lower alkylmercapto; an aromatic radical which has 6 to 12 carbon atoms and which can be optionally substituted by halogen, nitro, trihalogeno-lower alkyl (particularly trifluoromethyl), cyano, lower alkyl, lower alkoxy or lower alkylmercapto; or a heterocyclic radical having 5 or 6 ring atoms, it being possible for 1 to 3 hetero atoms (such as oxygen, sulphur and/or nitrogen) to be present in the ring system, and $R^2$ represents a straight or branched alkyl radical which has 1 to 6 carbon atoms and which can be optionally substituted by lower alkoxy, lower alkylmercapto, lower alkoxycarbonyl, halogen, cyano or nitro; an alkenyl radical having 3 to 6 carbon atoms; an alkinyl radical having 3 to 6 carbon atoms; a cycloaliphatic radical which has 5 to 8 ring carbon atoms and which can be optionally substituted by lower alkyl or lower alkoxy; or an araliphatic radical having 7 to 12 carbon atoms, it being possible for the aromatic ring system to be optionally substituted by one or more substitutents selected from lower alkyl, lower alkoxy, lower alkylmercapto, lower alkoxycarbonyl, halogen, cyano and nitro, comprising in a first stage reacting an N-substituted O-aryl N-chlorocarbonyl carbamate of the formula

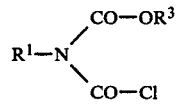

in which
$R^3$ represents a phenyl radical which can be optionally substituted by lower alkyl, lower alkoxy, halogen, halogeno-lower alkyl (particularly trifluoromethyl), cyano and/or nitro, or a naphthyl radical, with an isothiosemicarbazone of the formula

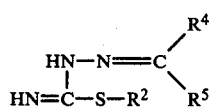

in which
$R^4$ represents a hydrogen atom or an alkyl radical having 1 to 3 carbon atoms, a cycloalkyl radical having 5 to 7 carbon atoms, or a benzyl or aryl radical having 6 to 10 carbon atoms, it being possible for each of the mentioned radicals to be substituted by halogen, cyano, nitro, lower alkyl, lower alkoxy or lower alkylmercapto, and
$R^5$ represents an alkyl having 1 to 3 carbon atoms, cycloalkyl having 5 to 7 carbon atoms, a benzyl or aryl radical having 6 to 10 carbon atoms, it being possible for each of the mentioned radicals to be substituted by halogen, cyano, nitro, lower alkyl, lower alkoxy or lower alkylmercapto, or
$R^4$ and $R^5$ together with the alkylidene C atom form a 5-membered to 7-membered carbocyclic ring. $R^4$ and $R^5$ particularly preferably represent methyl radicals, or a hydrohalide thereof, at a temperature between about 0° and 50° C. in the presence of an acid-binding agent, thereby to form open-chain intermediate products of the formula

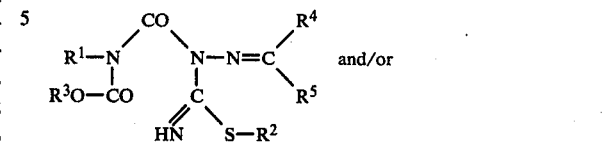 and/or

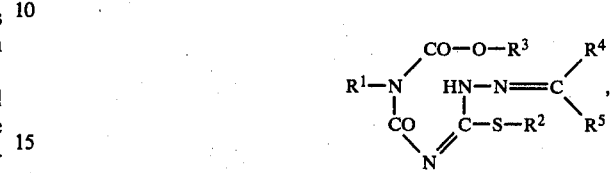

then heating the intermediate products in a second stage to a temperature between about 50° and 150° C. thereby to form a 1-alkylidene-amino-1,3,5-triazine-2,4(1H, 3H)-dione of the formula

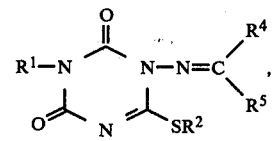

and in a third stage hydrolyzing the 1-alkylidene-amino-1,3,5-triazine-2,4(1H, 3H)-dione in an acid medium.

2. A process according to claim 1, wherein the first process stage is carried out at a temperature between about 5° and 35° C. and the second process stage is carried out at a temperature between about 70° and 120° C.

3. A process according to claim 1, wherein about 0.9 to 1.1 mols of the isothiosemicarbazone or hydrohalide thereof and about 1 or 2 mols of the acid-binding agent are used per mol of the O-phenyl N-chlorocarbonyl carbamate.

4. A process according to claim 1, wherein about 1 mol of the isothiosemicarbazone or hydrohalide thereof and about 1 or 2 mols of the acid-binding agent are used per mol of the O-phenyl N-chlorocarbonyl carbamate.

5. A process according to claim 1, wherein at least one of the first and second process stages is carried out in the presence of a diluent.

6. A process according to claim 1, wherein the reactants in the first stage are O-phenyl N-chlorocarbonyl-N-neopentyl carbamate and S-ethylacetoneisothiosemicarbazone, or a hydrochloride or hydrobromide thereof.

7. A process according to claim 6, wherein the first process stage is carried out at a temperature between about 5° and 35° C. and the second process stage is carried out at a temperature between about 70° and 120° C., at least one of the first and second process stages is carried out in the presence of a diluent, and about 1 or 2 mols of the acid-binding agent are used per mol of the O-phenyl N-chlorocarbonyl carbamate.

8. A process for the production of a cyclic compound of the formula

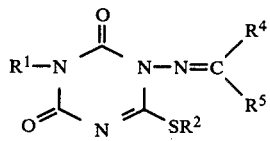 (V)

in which
- R¹ is an aliphatic, cycloaliphatic, araliphatic or aryl hydrocarbon radical, each of which is optionally substituted by halogen, nitro, alkyl, alkoxy; alkylmercapto, halogeno-alkyl, cyano, aryl, aryloxy and arylmercapto, or is a heterocyclic radical, and
- R² is an aliphatic, cycloaliphatic, or araliphatic hydrocarbon radical, rach of which is optionally substituted by halogen, cyano, nitro, alkyl, alkoxy, alkoxycarbonyl or alkylmercapto,
- R⁴ is hydrogen, or an alkyl, cycloalkyl, aralkyl or aryl radical each of which is optionally substituted by halogen, cyano, nitro, alkyl, alkoxy or alkylmercapto, and
- R⁵ is an alkyl, cycloalkyl, aralkyl or aryl radical each of which is optionally substituted by halogen, cyano, nitro, alkyl, alkoxy or alkylmercapto, or R⁴ and R⁵, together with the alkylidene C atom, form a 5-membered to 7-membered carbocyclic ring, comprising heating a compound of the formula

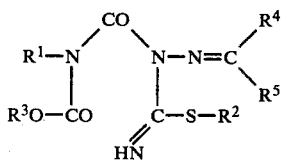 (IVa)

and/or

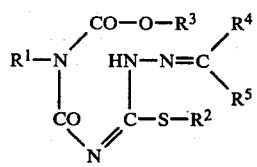 (IVb)

wherein
R³ is an aryl radical optionally substituted by alkyl, alkoxy, halogen, halogenoalkyl, cyano or nitro;
to a temperature between about 50° and 150° C., optionally in the presence of a diluent.

* * * * *